United States Patent [19]

Weinberger et al.

[11] Patent Number: Plant 7,574

[45] Date of Patent: Jul. 2, 1991

[54] HYBRID PLUM TREE CV. SUPLUMSIXTEEN

[75] Inventors: John H. Weinberger; Timothy P. Sheehan, both of Fresno, Calif.

[73] Assignee: Sun World, Inc., Indio, Calif.

[21] Appl. No.: 468,462

[22] Filed: Jan. 22, 1990

Related U.S. Application Data

[62] Division of Ser. No. 99,496, Sep. 21, 1987, abandoned.

[51] Int. Cl.[5] ..... A01H 5/00

[52] U.S. Cl. ..... Plt./38

[58] Field of Search ..... Plt./38; 800/200

[56] References Cited

U.S. PATENT DOCUMENTS

P.P. 5,413 3/1985 Paul ..... Plt./38

P.P. 5,662 2/1986 Bradford et al. ..... Plt./38

*Primary Examiner*—James R. Feyrer

*Attorney, Agent, or Firm*—William H. Elliott, Jr.

[57] ABSTRACT

A plum tree characterized by its large, early ripening dessert quality, red-black fruit which are ovate in shape with a pointed blossom end. Trees of the variety are of medium size and bear fruit regularly.

1 Drawing Sheet

This application is a division of our pending application Ser. No. 07/099,496, filed Sept. 21, 1987 now abandoned.

This invention relates to the discovery and asexual propagation of a new variety of hybrid plum tree, *Prunus salicina* Suplumsixteen. The tree is an early seasoned red-black plum cultivated for dessert fruit. It was discovered by John H. Weinberger and Timothy P. Sheehan in Fresno, Calif., and has as its seed parent Queen Rosa (unpatented) and, as its pollen parent, El Dorado (unpatented).

The new variety cv. Suplumsixteen may be distinguished from other presently available commercial plum cultivars by the following combination of characteristics: its large, early ripening dessert quality, red-black fruit, ovate in shape with a pointed blossom end; its medium-sized and regularly bearing tree; and its leaves which lack any undulation of their serrated margin and which bear a pair of globose-shaped glands on both the leaf base and petiole. The new variety holds these distinguishing characteristics through succeeding propagations by grafting.

Among the characteristics which distinguish the new variety of plum tree from its pollen parent, El Dorado, may be noted the following: The fruit of the new variety ripens two weeks earlier than that of the pollen parent. The fruit of Suplumsixteen is larger than that of El Dorado and is pointed at the apex. The skin of the fruit of the new variety exhibits more exterior red color than the skin of El Dorado.

The new variety may be distinguished from its seed parent, Queen Rosa, in the following combination of characteristics: Whereas the skin color of the fruit of the new variety is almost black in color, the skin color of Queen Rosa is red. The fruit of Suplumsixteen is smaller in size than that of Queen Rosa and is ovate in shape, as contrasted with the round shape of Queen Rosa. Fruit of Suplumsixteen ripens about one week earlier than does the fruit of Queen Rosa.

The accompanying drawing illustrates, in full color, a typical stem and leaves of the new plum tree and the ripe fruit as viewed from the stem end and in profile. The drawing also illustrates the fruit sectioned in half from end to end, one-half of the fruit shown with the stone in place in the flesh and the other half shown with the stone removed from the flesh.

Throughout this specification, color names beginning with a small letter signify that the name of that color, as used in common speech, is aptly descriptive. Color names with capital letters designate values based upon Munsell's Color Cascade, put out by Munsell Color Company.

Plum tree of the new cultivated variety Suplumsixteen have been deposited before the filing date of this application in an orchard located at 5090 East Church Avenue, Fresno, Calif. and are identified there by applicant's identification number 59-134.

The descriptive matter which follows pertains to plum trees of the new variety grafted onto Nemaguard TM rootstock and grown in the environment of the San Joaquin Valley, Calif. and is believed to apply to plants of the variety grown in similar conditions of soil and climate elsewhere.

TREE

The tree is of medium size and medium vigor. It is semi-upright in habit and tends to rounding of the head. The foliage tends towards medium dense growth. The hardiness has not been generally tested. The trees are medium producers, bearing their fruit regularly.

The trunk is of medium thickness and the bark medium in texture. The branches are medium in caliper and are of medium smoothness. The branches have a dull surface appearance and carry a medium number of medium-sized lenticels.

LEAVES

In general, leaves are of medium size, having an average length of about 11 cm. and an average width of about 4 cm. Leaves are elliptic in outline and upfolded in profile. Leaf blade tips curve downwardly and have an acute angle. The serrate leaf margin does not undulate. The leaf apex is acuminate; the leaf base is V-shaped. Leaves are of medium thickness. Leaf color on the upper surface is green, around 20-15 Munsell in color. The upper leaf surface is smooth, witn no hairs present and is of medium glossiness. The lower leaf surface is green, around 22-13 Munsell in color, weak in glossiness with no hairs present. The lower leaf surface is rugose in texture and has a dull surface appearance.

The petiole is of medium length and medium thickness. There are usually two medium-sized globose glands positioned on both the leaf base and petiole. Glands are brown in color. Stipules are deciduous.

Leaf buds are very small and conical in shape. Their position, relative to the shoot, is slightly held out and their support is not decurrent.

FLOWERS

Flowers are, in general, similar to those of other plum trees.

Flowers attain full bloom, on the average, around the first week of March.

FRUIT

The fruit, as now described, was eating ripe. The size of the fruit of that stage of its development is uniform in size, having an axial diameter of about 5 cm. and a transverse diameter in the suture plane of about 6 cm. At right angles to the suture plane, the measurement is about 6 cm., thus indicating a practically uniform, symmetrical and broadly ovate shape. The position of the maximum diameter is towards the stem end. The fruit is symmetric about the suture line. Fruit ripens early in season.

The suture is an inconspicuous shallow line extending from the base to the apex. The ventral surface is rounded slightly, with equal lips. The depression of the apex is indistinct. The pistil base does not persist. There is no pubescence at the apex.

The stem cavity is rounded, except that it is usually elongated in the plane of the suture, with the suture showing on one side. The depth of the cavity is about 1 cm., and its width about 1.5 cm. No markings are present. The base of the fruit is rounded and its apex is prolonged in shape. The pistil point is apical in shape.

The stem is of medium length and adheres with medium strength to the stone.

The skin, which is of medium thickness and of medium texture is tenacious to the flesh and shows no tendency to crack during the dry season. Skin color is red-black, around 45-15 Munsell. Down is wanting and a bloom is present. Skin is not reticulated but possesses some roughness. Skin is slightly acidic to taste.

The color of the flesh is yellow, around 25-3 Munsell, but the surface of the pit cavity is white to creamy, around Yellow 25-3 Munsell. The amygdalin content is moderate and juice was present in moderate amounts. The flesh has a medium sugar content. Flesh texture is medium and fibers are few in number. Fruit ripenes evenly to produce fruit of good eating quality. The flavor is delicate and the aroma wanting.

The stone clings, adhering to flesh over its entire surface. Fibers of the stone are short. The stone is of medium size, being about 2 cm. in length, and about 2 cm. in breath. The width at the stalk end of the stone is about 3 mm. and about 1 cm. in thickness. The angle of the stalk end is obtuse. The form of the stone in profile is generally elliptical. The form in ventral view is flattened. The stone's base is straight, its apex acuminate. The hilum is oblong. The position of the stone's maximum breadth is toward the middle and the sides are generally equal. The surface of the stone is regular and there is no outgrowing keel. The ridges are rounded towards the base. Pits are absent. The ventral stone edge is without a wing and the dorsal stone edge is narrow with narrow grooves. The color of the stone is light brown, around 32-5 Munsell. The stone had a slight tendency to split during the dry season.

The fruit is well adapted for market use and to serve as dessert. It has good resistance to insects and good shipping quality.

What is claimed is:

1. A new variety of plum tree, the variety being particularly distinguished and characterized by its large early-ripening dessert quality red-black fruit, ovate in shape with a pointed blossom and; its medium sized and regularly bearing tree; and its medium-sized elliptic leaves which lack any undulation of its serrated margin and which bear a pair of globose-shaped glands on both the leaf base and petiole substantially as herein shown and described.

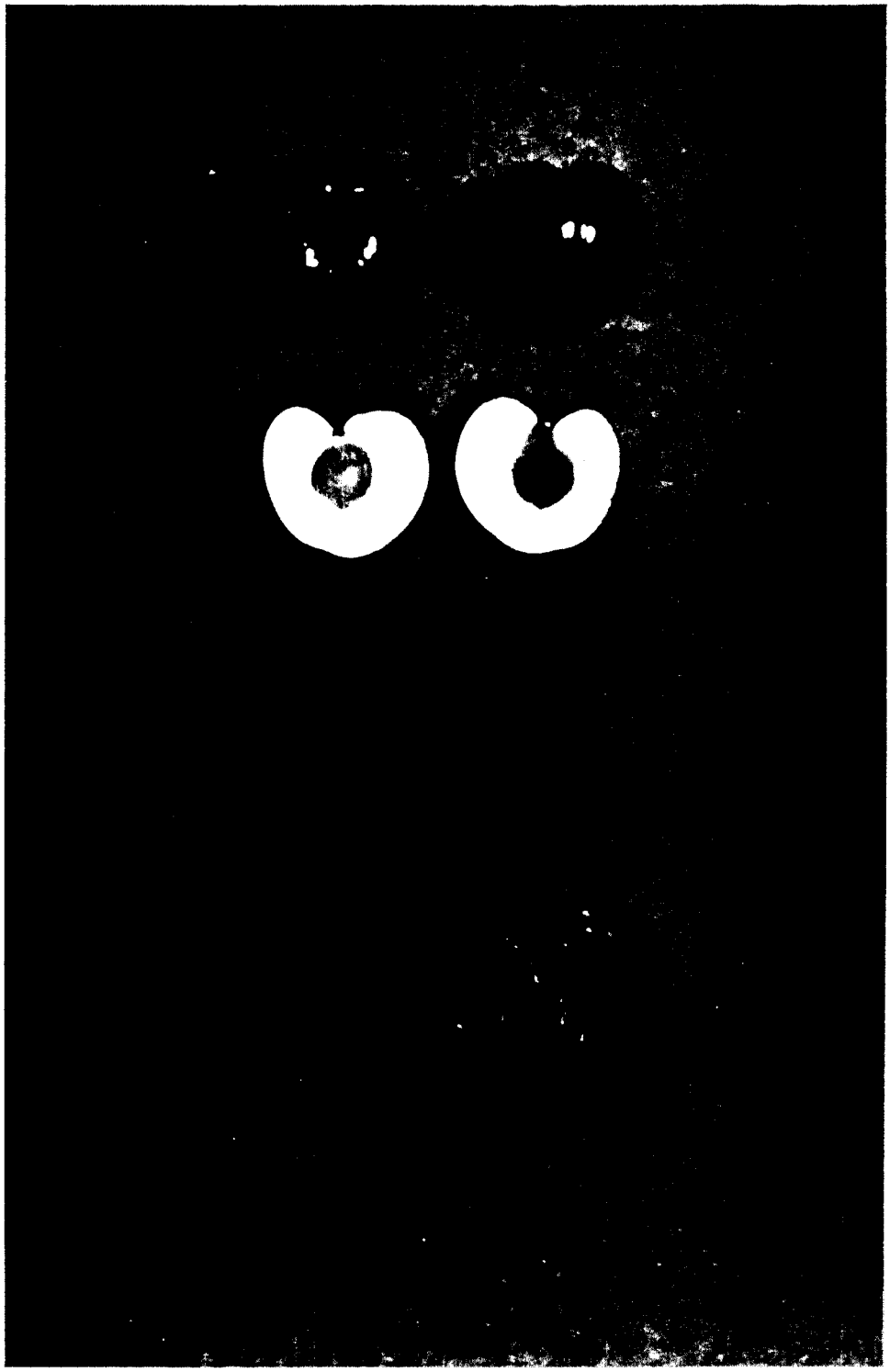

* * * * *